US00PP31137P2

(12) United States Plant Patent
Hansen

(10) Patent No.: US PP31,137 P2
(45) Date of Patent: Nov. 26, 2019

(54) **X *MANGAVE* PLANT NAMED 'SNOW LEOPARD'**

(50) Latin Name: **Hybrid; *Manfreda* times *Agave*, known as x *Mangave***
Varietal Denomination: Snow Leopard

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/501,208

(22) Filed: Mar. 6, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden

(57) ABSTRACT

A new and unique X *Mangave* plant named 'Snow Leopard' characterized by long arching succulent foliage with deep-green centers and variegated yellowish-cream to creamy-white margins and frosty green region between the margin and center. The leaves develop reddish to greyed-purple spotting and tinting under high ultraviolet light. Growth rate is moderate to rapid and the new plant has good natural pup production. The green flowers on tall stiff scapes are loaded with nectar are highly attractive to hummingbirds.

2 Drawing Sheets

Botanical classification: Hybrid; *Manfreda* times *Agave*, known as x *Mangave*.
Variety denomination: 'Snow Leopard'.

STATEMENT REGARDING PRIOR DISCLOSURES UNDER 37 CFR 1.77(B)(6)

The first non-enabling disclosure of the claimed plant, in the form of a private sale, was made by Walters Gardens, Inc. on Mar. 12, 3018 to Plant Delights Nursery, Inc. Plants for this sale were obtained from the inventor. Since then, on Feb. 14, 2019, the plant was first advertised on a website managed by Walters Gardens, Inc. No plants of x *Mangave* 'Snow Leopard' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Snow Leopard' that was discovered by the inventor at a wholesale perennial nursery in Zeeland, Mich., USA on Mar. 23, 2015 as a whole plant mutation in a tissue culture propagated batch of x *Mangave* 'Jaguar' (not patented). Through trials at the same nursery the plant was assigned the breeder code 15-SP-MAN-389. The new plant has been successfully asexually propagated first by removal of offsets and later by sterile shoot-tip tissue culture at the same nursery in Zeeland, Mich.. The asexual tissue culture propagation has been found to produce stable and identical plants that maintain all the unique characteristics of the original plant.

BRIEF SUMMARY OF THE INVENTION x *Mangave* 'Snow Leopard' differs from its parents as well as all other *Manfreda, Agave* and x *Mangave* known to the applicant. The mutation parent, 'Jaguar' has flexible arching foliage that has an olive-green color with greyed-purple spotting and without the near white leaf margins. Other similar cultivars include: 'Kaleidoscope' U.S. Plant Pat. No. 28,614, 'Carnival' copending U.S. Plant patent application Ser. No. 16/501,028 and 'Navajo Princess' U.S. Plant patent application Ser. No. 16/350,481. 'Kaleidoscope' has a creamy-yellow margin, more greyed-purple spotting and more orangish-red blush when grown in high ultraviolet light. 'Carnival' has the lighter creamy-yellow in the center of the leaf and the dark green along the margins. 'Navajo Princess' has foliage that is more oblanceolate and broader with larger marginal teeth and the leaf centers are lighter green colored and rarely offsets pups compared to the new plant.

The new plant, 'Snow Leopard', is unique from all of the above cultivars and all *Agave*, x *Mangave* and *Manfreda* known to the inventor by the following combined traits:

1. Medium mound of lanceolate to gladiate, semi-fleshy, foliage small flexible marginal teeth and flexible apex;
2. Leaves have creamy white margins with irregular frosty green zone between margin and deep-green center;
3. Foliage has reddish to greyed-purple spots an regions receiving strong ultraviolet light;
4. Foliage upright to outright;
5. Leaves flat when young and becoming slightly cupped in maturity;
6. Moderate to vigorous growth rate and good natural pup production.

BRIEF DESCRIPTION OF THE DRAWING

The photographs of x *Mangave* 'Snow Leopard' demonstrates the overall appearance of the new plant including the unique traits as a three-year-old plant grown in a container in a full-sun outdoor garden in Zeeland, Mich. with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
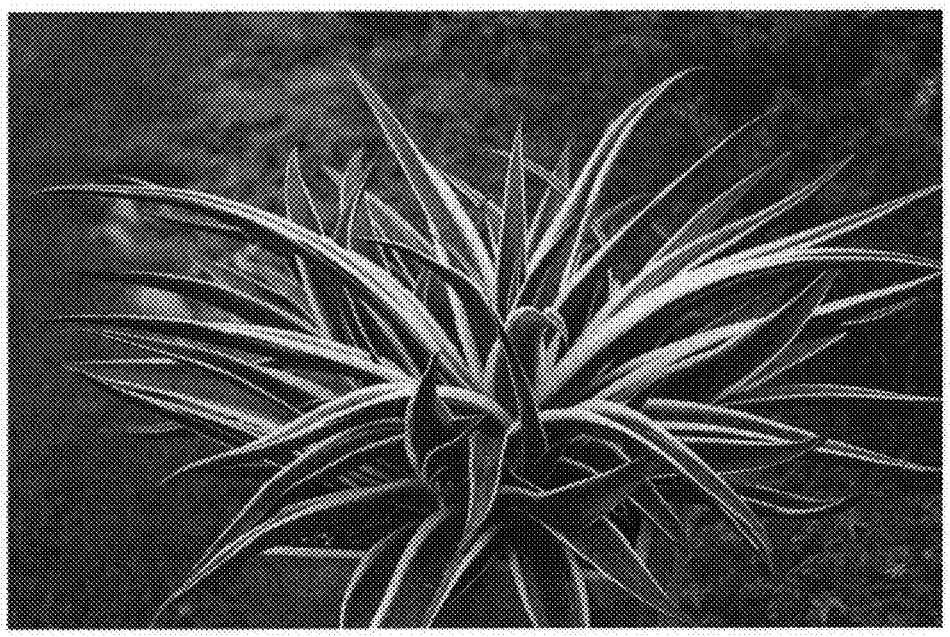
FIG. 1 shows a side view of a plant.
Figure 2:
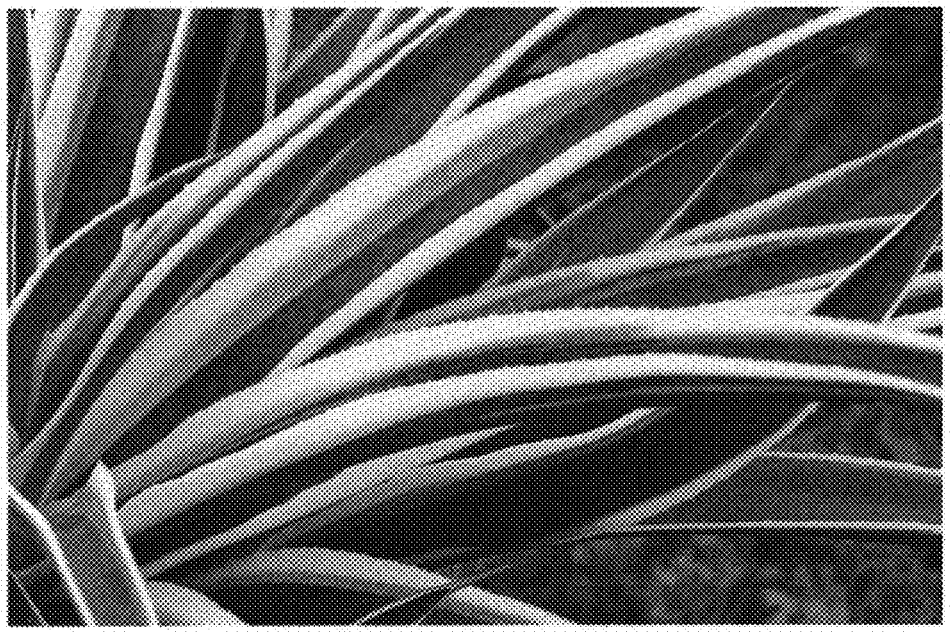
FIG. 2 shows a close-up of the foliage with small marginal teeth, creamy-white margins, dark green center and intermediate zone.
Figure 3:
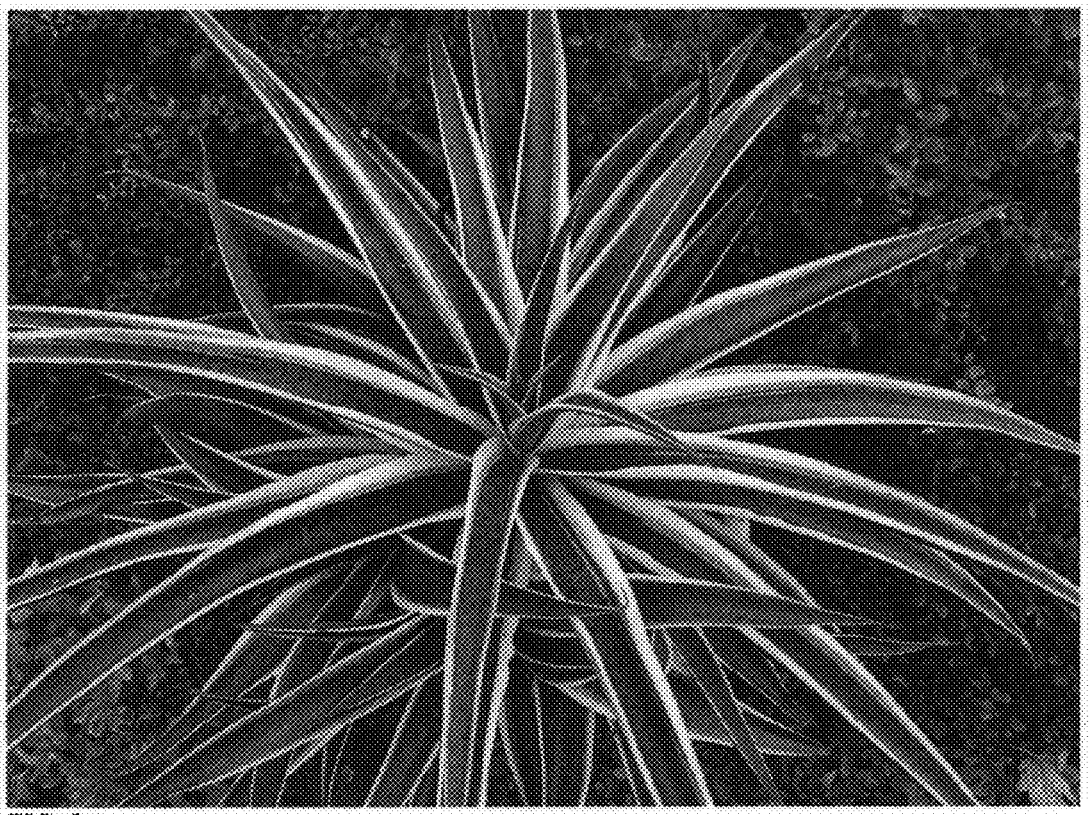
FIG. 3 shows a plant with natural pups grown in higher ultraviolet light for the summer season.

The following descriptions and color references are based on the 2015 edition of The Royal Horticultural Society Colour Chart except where common dictionary terms are used. The new plant, x *Mangave* 'Snow Leopard', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse and in a full-sun trial garden in Zeeland, Mich. with supplemental water and fertilizer as needed.

Propagation: By sterile shoot-tip tissue culture and removal of offsets;

Time to initiate roots from tissue culture: About 21 days;

Growth rate: Moderate to rapid;

Crop time: About 14 to 18 weeks to finish in a 3.8 liter container from a 35 mm tissue culture growing at about 21° C.;

Rooting habit: Fleshy, lightly branching, with roots up to 25 cm long;

Root color: Nearest RHS 158C;

Plant shape and habit: Succulent herbaceous perennial with basal rosettes of leaves radially emerging and arching from central rhizome, producing a symmetrical rounded mound;

Plant size: Foliage height about 40.0 cm tall from soil line to the top of the leaves and about 78.0 cm wide at the widest point at soil line;

Foliage description: Linear to lanceolate; simple, fleshy, glabrous; margins finely dentate with flexible teeth; apex narrowly acute, flexible; base truncate, sessile, clasping; adaxial and abaxial surface lustrous;

Number of leaves: About 60 per plant;

Leaf blades: Finely dentate; to about 46.0 cm long, about 50.0 mm wide at base and 4.0 mm thick, average about 42.5 cm long, 46.0 mm wide and 4.0 mm thick; usually bi-laterally symmetrical; glabrous and glaucous above and below; variegated with wide creamy white margin about 9.0 cm wide near middle; with intermediate lighter green zone between margin and center on older leaves of about 4.0 mm wide at widest point and irregular speckles of between about 1.0 diameter to about 3.0 mm across and about 6.0 mm long;

Foliage fragrance: None observed;

Leaf blade color:

*Adaxial* (*young*) *center*.—Between RHS NN137A and RHS 139A.

*Adaxial* (*young*) *margin*.—Nearest RHS 8C.

*Adaxial* (*young*) *intermediate*.—Nearest RHS 94B.

*Abaxial* (*young*) *center*.—Nearest RHS 146A.

*Abaxial* (*young*) *margin*.—Nearest RHS 8C.

*Abaxial* (*young*) *intermediate*.—Nearest RHS 94B.

*Adaxial* (*mature*) *center*.—Nearest RHS 139A.

*Adaxial* (*mature*) *margin*.—Nearest RHS 158C to RHS NN155A.

*Adaxial* (*mature*) *intermediate zone*.—Between RHS 189A and RHS 189B.

*Abaxial* (*mature*) *center*.—Blend between RHS 137A and RHS 139A.

*Abaxial* (*mature*) *margin*.—Between RHS NN137A and RHS 139A.

*Abaxial* (*mature*) *intermediate zone*.—Between RHS 191B and RHS 191C.

*Spots and marginal tinting in regions of high ultraviolet light exposure*.—On abaxial and adaxial margins nearest RHS 53B, on abaxial and adaxial centers nearest RHS N187A to RHS 187B.

Mucro: Absent;

Petiole: Sessile;

Veins: Parallel; not distinct;

Peduncle: Terete; glaucous; glabrous; stiff; strong; with cauline leaves nearly adpressed along surface; about 260 cm long and 2.0 cm diameter at base; attitude upwards, erect;

Peduncle color: With glaucous bloom nearest RHS N138A, without glaucous bloom nearest RHS 139A;

Pedicel: Terete; glaucous; glabrous; stiff; strong; about 1.7 cm long and 2.5 mm diameter;

Pedicel color: Nearest RHS 138A;

Cauline leaves: About 29 per scape; gladiate to lanceolate; simple, fleshy, glabrous; margins finely dentate with flexible teeth; apex acute with mucro; base truncate, sessile, clasping; proximally about 32.5 cm long and about 1.5 cm wide at base, decreasing distally; color adaxial and abaxial same as basal leaves;

Buds one day prior to opening: Elongated globose; terminal bulb about 2.6 cm long and about 1.0 cm across; proximal tube about 2.4 cm long and 6.0 mm across; overall about 5.0 cm long;

Bud color: Nearest RHS 138A;

Flower description: Perfect, actinomorphic; about 11.0 cm long and opening to about 5.0 cm across at outside of anthers; lasting about 3 to 4 days per flower; flowering period about three weeks in late winter in Michigan greenhouse; producing abundant nectar; approximately 75 flowers per scape; attitude mostly upright;

Flower fragrance: Faintly sweet;

Tepals: Six; glaucous abaxial; glabrous both adaxial and abaxial; acute apex and fused base; in two sets of three; outer set about 2.8 cm long and about 5.0 mm wide at base; inner set about 2.8 cm long and 4.0 mm wide at base; inner set creased along edge where overlapped with outer set while in bud;

Tepal color: Outer set adaxial nearest RHS 146B, abaxial nearest RHS N138C with glaucous bloom and nearest RHS 138A with glaucous bloom removed; inner set adaxial nearest RHS 146A and margin between RHS 146A and RHS 144A, and abaxial nearest RHS N138C with glaucous bloom and nearest RHS 138A without glaucous bloom and nearest RHS 144A along creased margin;

Androecium: Six;

*Filaments*.—Six; stiff and straight; about 7.0 cm long and 2.0 mm diameter at base; color between RHS 145C and RHS 160C with dense speckling of nearest RHS 182A.

*Anther*.—Dorsifixed; longitudinal; about 2.2 cm long and 1.0 mm diameter before opening; after dehiscence curving backward; color nearest RHS 165A.

*Pollen*.—Abundant; color nearest RHS 18A.

Gynoecium: Single;

*Style*.—5.5 cm long and 2.0 mm diameter at base; color blend between RHS 145C and RHS 160C with dense speckling of RHS 184A.

*Stigma*.—Globose, apex tri-lobed; about 2.5 mm tall and 3.0 mm across top; color side and top between RHS 177A and RHS 187A; top stigmatic surface in tri-pointed star with color nearest RHS 194B.

*Ovary*.—Inferior.

Fruit: Dehiscent, tri-valved, loculicidal capsule; apex abruptly acute; base slightly tapered; about 3.5 cm long and 1.7 cm across;

Fruit color: When immature nearest RHS N138A; at dehiscence blend between RHS 199C and RHS 161B;

Seed: Flattened, near round; about 5.0 mm across and about 1.0 mm thick; color nearest RHS 202A;

Disease resistance: X *Mangave* 'Snow Leopard' has not been observed to be resistant to diseases common to other X *Mangave* beyond that which is normal for *Agave* or *Manfreda*. The plant is xeromorphic and survives well with minimal water once established. Hardiness at least from USDA zone 8 to 11. Full extent of winter hardiness has not been tested.

I claim:

1. A new and distinct cultivar of ornamental X *Mangave* plant named 'Snow Leopard' as herein described and illustrated, suitable as a potted plant or for the garden.

* * * * *